(12) United States Patent
Koppany

(10) Patent No.: US 7,427,137 B2
(45) Date of Patent: Sep. 23, 2008

(54) VISUAL ACUITY TESTING

(76) Inventor: Robert Koppany, 4840 W. 123rd St., Hawthorne, CA (US) 90250-3514

(*) Notice: Subject to any disclaimer, the term of this patent is extended or adjusted under 35 U.S.C. 154(b) by 0 days.

(21) Appl. No.: 11/489,031

(22) Filed: Jul. 18, 2006

(65) Prior Publication Data
US 2008/0018857 A1    Jan. 24, 2008

(51) Int. Cl.
A61B 3/02 (2006.01)
A61B 3/00 (2006.01)

(52) U.S. Cl. .................... 351/239; 351/246
(58) Field of Classification Search ......... 351/205–223, 351/239, 241–246
See application file for complete search history.

(56) References Cited

U.S. PATENT DOCUMENTS

| | | |
|---|---|---|
| 1,879,833 A | 9/1932 | Tillyer et al. ............ 351/239 |
| 1,999,054 A | 4/1935 | Lee ........................ 351/239 |
| 4,854,695 A | 8/1989 | Lewis ..................... 351/246 |
| 4,968,131 A | 11/1990 | Lewis ..................... 351/239 |
| 5,129,720 A * | 7/1992 | Jovicevic ................ 351/243 |
| 5,416,540 A * | 5/1995 | Hayashi .................. 351/239 |
| 5,568,209 A * | 10/1996 | Priester et al. .......... 351/243 |
| 5,880,814 A | 3/1999 | McKnight et al. ........ 351/239 |
| 6,142,631 A | 11/2000 | Murdoch et al. ......... 351/239 |
| 6,379,007 B1 | 4/2002 | Farb ...................... 351/239 |
| 6,808,267 B2 * | 10/2004 | O'Neil et al. ............ 351/246 |

* cited by examiner

*Primary Examiner*—M. Hasan
(74) *Attorney, Agent, or Firm*—Billy A. Robbins; Connolly Bove Lodge & Hutz LLP

(57) ABSTRACT

Eye chart for testing visual acuity which includes a plurality of optotypes arranged in a plurality of lines with each optotype in a line having a uniform resolution throughout and the resolution for each optotype in a given line is the same. The optotypes are generated by standardizing the maximum resolution angle any one letter may have and such is done by utilization of a design circle which represents the maximum resolution.

11 Claims, 3 Drawing Sheets

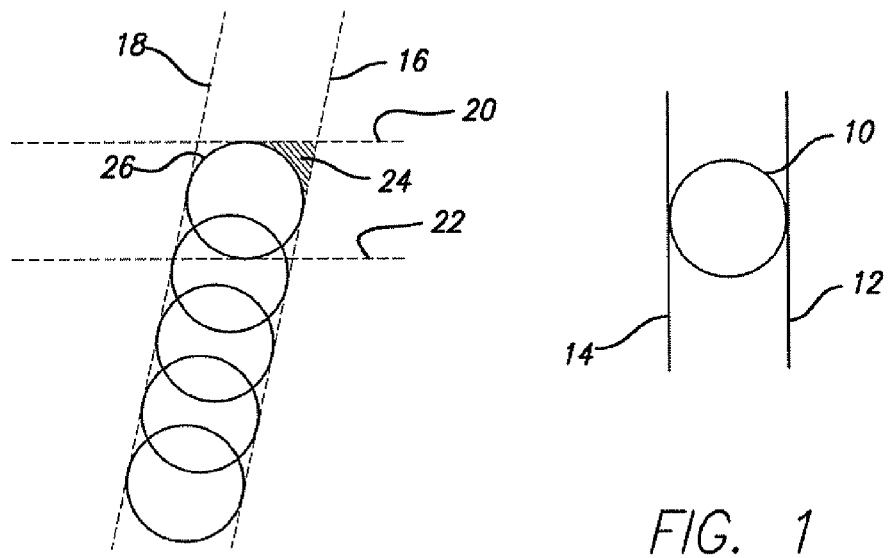
FIG. 1
FIG. 2
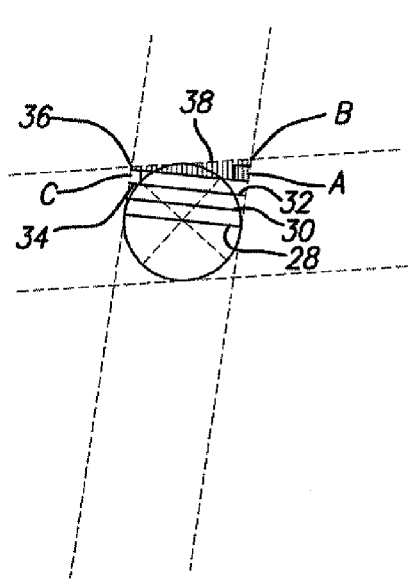
FIG. 3
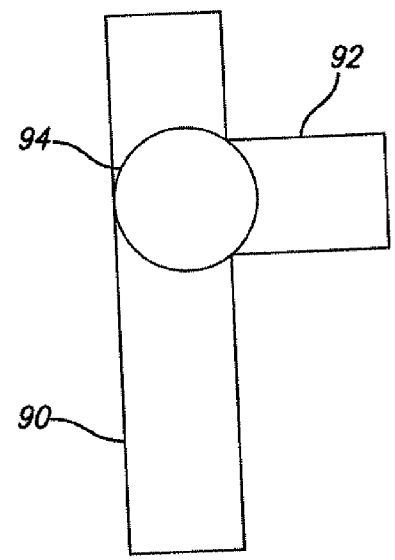
FIG. 4

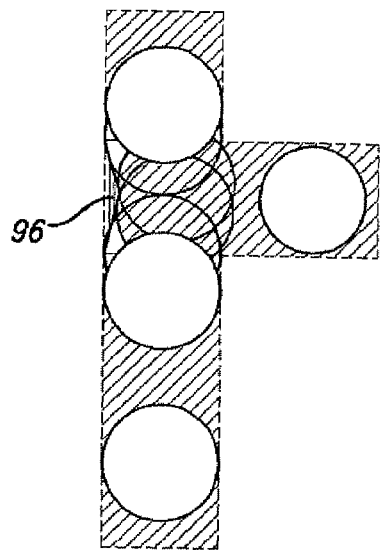
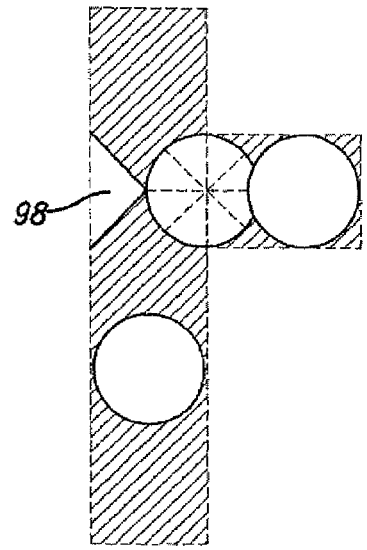
FIG. 5       FIG. 6
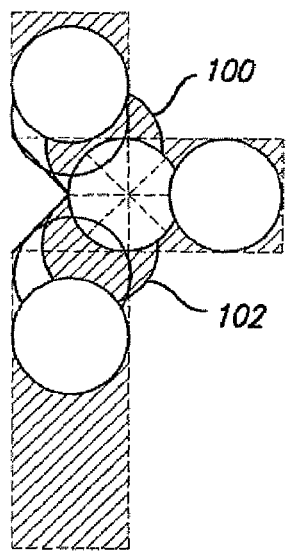
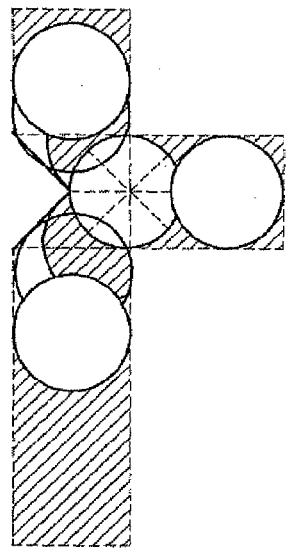
FIG. 7       FIG. 8

FIG. 9

AH DISTINCTLY I REMEMBER IT WAS IN THE BLEAK DECEMBER AND EACH SEPARATE DYING EMBER WROUGHT ITS GHOST UPON THE FLOOR EAGERLY I WISHED THE MORROW VAINLY I HAD SOUGHT TO BORROW FROM MY BOOKS SURCEASE OF SORROW SORROW FOR THE LOST LENORE FOR THE RARE AND RADIANT MAIDEN WHOM THE ANGELS NAME LENORE NAMELESS HERE FOREVERMORE

VISUAL ACUITY TESTING

FIELD OF THE INVENTION

The present invention relates to eye charts used for measuring the visual acuity of a subject and the method of testing such visual acuity utilizing the eye charts of the present invention.

BACKGROUND OF THE INVENTION

Since the early development by Snellen of his acuity test in 1862, optotypes and combinations thereof, including both letters and numbers, have been used for visual acuity testing. Such testing is necessary for determination of lens correction, detection of impairment of vision, assessment of the effects of medical or surgery therapy, screening testing, qualifying testing, determining the degree of observation of spatial detail and the like. In each instance, the various systems and optotypes which attempt to improve the standardization of acuity testing by the use of various letters or designs are limited in uniformity by having variability of optotype recognition difficulty.

When utilizing the visual acuity charts, which have been developed to date, it is recognized that accuracy depends upon whether the chart letters are equally legible or whether some blur interpretation may be characteristic of the configuration of some of the letters. For example, it may be difficult for a patient to distinguish between the letters "C" and "G." In addition, the details of the symbols may blur as the distance from the eye increases and identification thus becomes more difficult. As a result, a clinician giving the test may credit the person taking the vision test with accurately identifying similar symbols and other times such clinicians may only give credit for identifying the exact symbol accurately. Thus, there is a subjective judgment which leads to inconsistent quantification of visual acuity. This results, in great part, because the resolution limits of the optotypes used for the visual acuity testing are not consistent. This inconsistency leads the patient to guessing what appears on the eye test chart.

There is thus a need for a visual acuity testing system and method utilizing optotypes which have a uniform resolution for all of the optotypes at the same size and distance.

SUMMARY OF THE INVENTION

An eye chart for testing visual acuity which includes a plurality of optotypes arranged in a plurality of lines with each line representing a particular visual acuity and each optotype in a line having a uniform resolution throughout and the resolution for each optotype in a given line is the same.

The invention also includes the method of testing a patient by providing an eye chart having the plurality of optotypes as above defined and having the patient identify the optotypes which appear in a given line on the eye chart and recording the results of the patient's recognition.

BRIEF DESCRIPTION OF THE DRAWINGS

FIG. 1 illustrates the use of the maximum containment circle;

FIG. 2 illustrates the utilization of the maximum containment circle with regard to the corner of an obliquely angled portion of an optotype;

FIG. 3 illustrates the manner in which the obliquely angled portion of the letter exceeds the maximum containment circle diameter;

FIG. 4 illustrates the manner in which an inscribed circle at the junction of an ascender and counter is greater than the constant containment circle;

FIG. 5 is illustrative of the manner in which an indentation is formed at the junction of an ascender and counter maintained the desired resolution;

FIG. 6 is illustrative of the required indentation at the junction of the ascender and counter to assure that the maximum containment circle is not compromised;

FIG. 7 is illustrative of the maximum containment circles extending beyond the boundaries of the intersection of an ascender and counter;

FIG. 8 illustrates the manner in which the maximum containment circles extending beyond the letter are removed; and FIG. 9 is illustrative of an eye chart having optotypes formed utilizing the maximum containment circle as described in the present invention and in which there is a substantially constant resolution throughout each letter in each line.

DETAILED DESCRIPTION

The present invention provides optotypes which can be used in an eye chart with resolution differences typically less than 1% between differing letters as opposed to the large resolution angle variation that occurs on many eye charts currently in use and disclosed in the prior art. These optotypes have been designed by standardizing the maximum resolution angle any one letter may have. To accomplish this very small resolution difference, the present invention utilizes a design circle which represents the maximum resolution any one letter in the eye chart may have.

By referring now more particularly to FIG. 1, the design circle 10 is illustrated within a pair of lines 12 and 14 which are illustrative of the boundaries of a portion of a letter which may be utilized within an eye chart. In designing the optotypes for use in the eye chart, a critical limitation is that no one letter would have any portion thereof which exceeds the area of the design circle 10. If the design circle is smaller than that shown in FIG. 1, then the patient viewing the eye chart would perceive the optotype as white or black depending on the immediate surrounding area.

As will be readily understood by those skilled in the art, when utilizing optotypes, particularly those comprised of letters, the arms of the optotypes are not always precisely vertical as is illustrated in FIG. 2. As a result, when the arms of the optotypes are other than precisely vertical or when there are intersecting vertical members and other members or arms at any angle and intersecting vertical members (ascenders) and horizontal arms (counters) of the optotype, the optotype, unless modified, will exceed the area of the design circle thus creating a situation where the desired resolution cannot be obtained. Illustrative of one such problem is set forth in FIG. 2 which shows in dotted lines the manner in which an obliquely-angled arm of an optotype at the upper terminus thereof would create a situation in which the desired resolution could not be obtained. As is shown in FIG. 2, the dotted lines 16 and 18 are illustrative of an obliquely-angled arm of an optotype, the deviation from perfectly vertical can be determined by reference to the horizontal lines 20 and 22. By assuming that the upper terminus of the optotype obliquely-angled arm is at the upper horizontal line 20, it can be seen that there is an extra space 24 next to the containment circle 26.

By reference to FIG. 3 it is noted that if one draws a line as shown at 28, which is equivalent to the diameter of the containment circle 26 and moves that line upwardly as shown at 30, 32 and 34 until the upper left corner 36 of the obliquely-angled arm of the optotype is reached, then the top edge 38 of the optotype becomes the hypotenuse for a right triangle shown at A B C. If corrective action is not taken, then this would result in the corner lines being longer than the others in the obliquely-angled arm of the optotype. Such would account for approximately a 15% error deviation from the containment circle thus exceeding the desired resolution. This, however, can be remedied by rounding the corner edges so that no part of the obliquely-angled arm of an optotype exceeds the containment circle.

By reference now to FIG. 9, which shows text without punctuation for an impromptu eye chart utilizing optotypes in the form of letters designed in accordance with the present invention, it becomes evident that the bottom of the angled arms of the letter A, as shown at 40 and 42, must also be rounded. Also, the arms of the letter K as shown at 44 and 46 must be rounded to maintain the required resolution. The top arms of the letter V, as shown at 48 and 50, must also be rounded since these two arms are also obliquely angled. Although the letter X is not shown in FIG. 9, it will be obvious to those skilled in the art that the terminus of each of the arms of the letter X must also be rounded since the two arms of the optotype of the letter X are obliquely angled as above described. In addition, the top arms of the letter Y, as shown at 52 and 54, must also be rounded.

Upon a further examination of the optotypes constructed in accordance with the present invention, it will also become evident that an area of error will occur when two corner lines of the optotype come together. To maintain the maximum resolution angle when such occurs, the corners on the outer edge must also be rounded so that they would inscribe the containment circle. For example, such must be done at the top of the letter A, as shown at 56. In addition, the upper and lower left corners of the letter D must also be rounded as shown at 56 and 58. It will also be noted that the upper and lower left corners of the letter D must also be rounded as shown at 60 and 62. A similar rounding of the upper and lower left corners of the letter E are required as shown at 64 and 66. In addition, the upper and lower left corners of the letter G must also be rounded as shown at 68 and 70. The top left corner of the letters R, F and P must also be rounded to accommodate the containment circle, such as illustrated at 72, 74 and 76. In addition, the lower left-hand corner of the letter L, as shown at 78, would have to be rounded. On the letter M, the upper left and right corners must also be rounded as shown at 80 and 82. The bottom of the V would also have to be rounded as shown at 84 as would the left and right bottom portions of the letter W as shown at 86 and 88.

It will thus be recognized that by rounding the various portions of the optotypes which include an obliquely-angled arm or where two corner lines come together, the optotypes in the form of the letters maintain their position within the containment circle, thus retaining the maximum resolution angle.

The maximum error in the containment circle arises from the area where two lines come together other than at the corners. Thus, where an ascender and a counter intersect, there is an error of approximately 26% larger than the size of the standardized containment circle which is used to construct the optotypes in accordance with the principles of the present invention. By reference now to FIGS. 4 through 8, such is illustrated as well as the manner in which the optotype may be modified so that the optotypes where an ascender and counter intersect will not exceed the containment circle and thus the desired resolution will be retained. As is shown in FIG. 4, an ascender 90 and a counter 92 intersect. When such occurs, a containment circle, as shown at 94, will exist at that intersection. As is evident to any observer, the circle 94 exceeds the maximum containment circle 10 as shown in FIG. 1 by a substantial amount. Unless the region where the ascender and counter intersect is modified, one would have the 26% error above referred to. As shown in FIG. 5, if the ascender is indented by approximately 15%, as is illustrated at 96, there is then provided a constant containment circle for the ascender; however, the containment circle for the counter still exceeds the desired amount. As a result, the indentation must go approximately halfway across the ascender as shown in FIG. 6 at 98. Any lesser indentation would result in a containment circle larger than that which is desired when the containment circle 10 is considered as illustrated in FIG. 1. When such is done, however, as is illustrated in FIG. 7, the containment circle extends beyond the boundaries of the ascender and counter as shown at 100 and 102. These extensions should be eliminated in order to make the optotype appear appropriately and such is illustrated in FIG. 8. Such produces a smaller resolution angle at this intersection of the ascender and the counter but such cannot be avoided in order to keep the maximum containment circle from being compromised. This assures that the resolution angle will never exceed the maximum containment circle.

When the required indentation at the intersection of the ascender and the counter is considered, it will be recognized by those skilled in the art that where intersecting members come together even if such is at angles different than ninety degrees, the optotypes at the point of intersection must be indented to maintain the required resolution. For example, the connecting lines for the letter A must be indented as is shown at 104 and 106 in FIG. 9. In addition, the indentations at the intersection of the ascender and the counter for the letter H must be indented as is illustrated at 108 and 110. Furthermore, where the connecting lines at the upper left and lower right in the letter N come together, there must also be indentations as shown at 112 and 114. It will also be recognized that on the left side of the letters E, F and P, such an indentation must be made as is shown at 116, 118 and 120. As is shown at 122, the ascender for the letter K must also be indented at the intersection of both of the arms for the letter K. At the top, center of the letter T, as shown at 124, there must be an indentation where the ascender and counter intersect and a similar indentation is required as shown at 126 at the top of the letter M, where the ascender and the counter intersect. Furthermore, where the ascender and counter intersect for the letter R, as shown at 128 and 130, there must be an indentation as is also the case at the bottom of the W as shown at 132. A similar indentation is also required where the intersection of the arms for the letters X and Q, although not shown in FIG. 9, come together. As is also illustrated in FIG. 9, there is a slight indentation at 134 where the ascender is intersected by the two arms of the Y.

Once these modifications to the optotypes in the form of letters are made, the letters all have a constant maximum resolution angle between them not exceeding a 2% variation and typically less than 1%. Such would eliminate guessing that an H is an N and other substitutions by the patient based on large resolution angle errors. It should be noted that the letters can be formed into sentences without punctuation such as is done in FIG. 9 and when such is done, the chart is not clear to the viewer at all until their minimum resolution visual acuity is reached, and then they can read the whole sentence. Although FIG. 9 is presented as such a visual acuity chart where sentences without punctuation are presented, it would be understood by those skilled in the art that letters may be selected as is done in other eye charts which are not in sentence form, but are merely letters. As an example, there are advantages for utilizing this optotype for the letters C, D, H, I, J, L, O, P, T and U where the patient could not see these letters if their angle of resolution was less than the thickness of the letters. With the letters B, E, F, G, M, S and W, there are multiple horizontal or vertical lines with the same resolution. Astigmatism may be assessed by using letters with non-horizontal or non-vertical lines, such as the A, V, X and Y with K, N and Z being of help. However, there could be problems with the viewer identifying the shape of the K, Q, N, R and Z being of some unfamiliarity to the viewer by their design when modified in accordance with the teachings of the present invention. It will be recognized by those skilled in the art that the size of the optotypes in each row may vary to accommodate the standard Snellen sizes. As the lines progress down the chart, the optotype sizes decrease as is well known.

In carrying out the testing of the visual acuity of a patient, the doctor or clinical technician would be provided an eye chart having optotypes designed in accordance with the principles of the present invention thereon and would present the same to the patient. The patient would then view the optotypes on the eye chart and identify one or more of the optotypes on the eye chart for the doctor or the clinical technician. Through such identification, the doctor or clinical technician would then be able to determine the patient's visual acuity.

There has thus been described an eye chart and the method of utilizing the same wherein the eye chart is comprised of optotypes constructed using a design circle which represents the maximum resolution any one letter can have and where no one letter will exceed this area for anywhere within the single letter and where all of the optotypes on a line are the same and where each optotype in the line has a uniform resolution throughout and the resolution for each optotype in a given line is substantially the same.

What is claimed is:

1. A system for testing visual acuity of a patient by presentation of a series of optotypes, comprising:
    means for presenting a plurality of optotypes arranged in a plurality of lines, each line representing a particular visual acuity,
    each optotype in a line having a uniform resolution throughout and the resolution for each optotype in a given line is the same;
    said uniform resolution is measured by a maximum containment circle in that no part of any optotype exceeds the area of the maximum containment circle; and
    the terminal portions of any optotype extending beyond a maximum containment circle confined within the optotype are rounded off to eliminate such extension.

2. A system as defined in claim 1 wherein the terminal portions of all obliquely angled optotypes are rounded off.

3. A system as defined in claim 2 wherein the bottom of the A, the arms of the K, the top of arms of the V, all arms of the X and the top arms of the Y are each rounded off.

4. A system as defined in claim 1 wherein the terminal portions of optotypes wherein two corner lines come together are rounded off.

5. A system as defined in claim 4 wherein the top of the A; the upper left and bottom left corners of the B, D, E and G; the top left corner of the R, F and P; the lower left corner of the L; the upper left and right corners of the M; the bottom of the V; and the left and right bottoms of the W are each rounded off.

6. A method of testing a patient's visual acuity comprising:
    providing a system according to claim 1;
    and the patient responding by identifying at least one of the optotypes presented by the means.

7. A system for testing visual acuity of a patient comprising:
    means for presenting a plurality of optotypes arranged in a plurality of lines, each line representing a particular visual acuity;
    each optotype in a line having a uniform resolution throughout and the resolution for each optotype in a given line is the same, the uniform resolution is measured by a maximum containment circle in that no part of any optotype exceeds the area of the maximum containment circle; and
    said optotypes have a constant maximum resolution angle between them not exceeding a two percent variation.

8. A system as defined in claim 7 wherein optotypes include an ascender and a counter which intersect, said ascender being indented at said intersection by an amount sufficient to maintain said resolution.

9. A system as defined in claim 8 wherein the ascender of optotypes represented by the letters H, E, F, P, and R are indented.

10. A system as defined in claim 7 wherein optotypes include an ascender and a counter which intersect, said counter being indented at said intersection by an amount sufficient to maintain said resolution.

11. A system as defined in claim 10 wherein the counter on the optotypes represented by the letters M, W, R and T is indented.

* * * * *